United States Patent [19]
Kambara et al.

[11] Patent Number: 5,968,331
[45] Date of Patent: Oct. 19, 1999

[54] SAMPLE HOLDING DEVICE FOR ELECTROPHORESIS APPARATUS AND SAMPLE INJECTION METHOD

[75] Inventors: Hideki Kambara, Hachiouji; Satoshi Takahashi, Kunitachi; Takashi Anazawa, Kokubunji; Takashi Yamada, Setagaya-ku, all of Japan

[73] Assignee: Hitachi, Ltd., Tokyo, Japan

[21] Appl. No.: 08/554,808

[22] Filed: Nov. 7, 1995

[30] Foreign Application Priority Data

Nov. 11, 1994 [JP] Japan .................................. 6-277777

[51] Int. Cl.⁶ ..................... G01N 27/26; G01N 27/447
[52] U.S. Cl. ..................... 204/450; 204/453; 204/455; 204/456; 204/466; 204/467; 204/600; 204/604; 204/605; 204/606; 204/616; 204/618
[58] Field of Search ..................... 204/601, 602, 204/603, 604, 605, 606, 607, 608, 609, 610, 612, 613, 614, 615, 616, 617, 618, 619, 620, 621, 600, 450, 451, 452, 453, 454, 455, 456, 461, 465, 466, 467

[56] References Cited

U.S. PATENT DOCUMENTS

| | | | |
|---|---|---|---|
| 3,616,387 | 10/1971 | Siebert et al. | 204/466 |
| 3,839,183 | 10/1974 | Klein et al. | 204/606 |
| 3,915,652 | 10/1975 | Natelson | 23/259 |
| 3,932,229 | 1/1976 | Grandine | 204/466 |
| 4,061,561 | 12/1977 | Fletcher et al. | 204/616 |
| 4,188,986 | 2/1980 | Wetterlin et al. | 141/130 |
| 4,827,780 | 5/1989 | Sarrine et al. | 204/608 X |
| 4,882,127 | 11/1989 | Rosenthal et al. | 422/50 |
| 5,104,512 | 4/1992 | Gombocz et al. | 204/607 |
| 5,192,412 | 3/1993 | Kambara et al. | 204/618 X |
| 5,217,591 | 6/1993 | Gombocz et al. | 204/466 |
| 5,284,565 | 2/1994 | Chu et al. | 204/619 |
| 5,346,603 | 9/1994 | Middendorf et al. | 204/618 X |
| 5,366,608 | 11/1994 | Kambara | 204/603 |
| 5,405,516 | 4/1995 | Bellom | 204/466 |
| 5,541,420 | 7/1996 | Kambara | 204/605 X |

FOREIGN PATENT DOCUMENTS

| | | |
|---|---|---|
| 5-27177 | 3/1993 | Japan . |
| 6-138037 | 5/1994 | Japan . |

OTHER PUBLICATIONS

Nature, vol. 361 (1993) pp. 565–566 "Multiple–sheathflow capillary array DNA analyser" by Hideki Kambara, et al.

Nature, vol. 359 (1992) pp. 167–169 "Capillary array electrophoresis: an approach to high–speed, high–throughput DNA sequencing" by Richard Mathies, et a.

Bio/Technology, vol. 6 (1988) pp. 816–821 "Optimization of Parameters in a DNA Sequenator Using Fluorescence Detection" by Hideki Kambara, et al.

*Primary Examiner*—Robert J. Warden, Sr.
*Assistant Examiner*—John S. Starsiak, Jr.
*Attorney, Agent, or Firm*—Antonelli, Terry, Stout & Kraus, LLP

[57] ABSTRACT

A sample holding device for electrophoresis apparatus according to the present invention wherein a plurality of sample holding capillaries are laid out in an array and are immobilized to the supporting jig. This sample holding device is configured to ensure the lower ends of the capillaries can contact the sample injection portion of the electrophoresis separation part of the electrophoresis apparatus, and provides easy sample injection and prevents the gel capillaries of the electrophoresis separation part from being damaged when sample holding capillaries are filled with gels, thereby allowing repeated use of the gel capillaries of the electrophoresis separation part.

72 Claims, 7 Drawing Sheets

SAMPLE HOLDING DEVICE FOR ELECTROPHORESIS APPARATUS AND SAMPLE INJECTION METHOD

BACKGROUND OF THE INVENTION

The present invention relates to the gel electrophoresis separation apparatus to analyze DNA, RNA or protein, and particularly to the sample holding device for fluorescence detection type DNA sequencer or the like, and to the sample injection method thereof.

DNA analysis uses gel electrophoresis. In recent years, there has been a widespread use of the apparatus which determines DNA sequences by fluorescence labeling of DNA and analyzing the DNA fragment length in real time. According to this apparatus, 0.1 mm to 0.3 mm thick polyacrylamide gel is formed in the gap between two sheets of glass, and is used as separation medium. Part of the gel top is made undulating to form sample injection wells. The sample is injected by the microsyringe into concave wells formed between sheets of glass.

In recent years, on the other hand, attention has been drawn to the method of using as separation medium the capillary gel, i.e. the gel formed in the capillary, in place of the slab gel. This is because high speed migration is enabled by providing high electric field since the capillary gel does not produce large joule's heat. Furthermore, electrophoresis systems provided with a great number of capillary gels have been developed. Such systems are disclosed, for example, in i) Kambara et al; Nature, vol. 361 (1993), pp. 565–566, ii) Mathies et al; Nature, vol. 359 (1992), pp. 167–169, iii) Takahashi et al; Japanese Patent Laid-Open 6-138037 (May 20, 1994) and iv) Takahashi et al; U.S. patent application Ser. No. 08/337,412 (Pending). According to this method, one end of the capillary is placed into the sample container, and voltage is applied between that end and another end of the capillary, thereby injecting DNA into the capillary by employing an electric field. Furthermore, v) Kambara; Japanese Patent Laid-Open-5-72177 (1991), vi) Kambara; U.S. Pat. No. 5,277,780 (Jan. 11, 1994) and vii) Kambara; U.S. Pat. No. 5,366,608 (Nov. 22, 1994) disclose an electrophoresis system wherein the capillary gels are connected to the sample injection holes at the side opposite to the sample injection side of the sample injection holes with which there is provided the sample injection plate having a great number of sample injection holes through which a great number of samples are injected.

Furthermore, viii) Kambara et. al; Bio/Technology, vol. 6 (1988), pp. 816–821 and ix) Kambara et. al; U.S. Pat. No. 4,971,677 (Nov. 20, 1990) show how the DNA fragments migrate in the gel.

The progress of genome analysis has come to require a great deal of the DNA base sequence determinations. This has resulted in the development of a DNA sequencer using the slab gel provided with a great number of migration lanes in the slab, and devices having many migration lanes with a great many capillaries arrayed. Despite increasing quantity of analysis, however, there has been a disadvantage of requiring much time and labor for the analysis, since the sample injection method has not been improved. Namely, in the slab gel apparatus, a great number of samples are injected one after another into the well by means of a microsyringe, requiring much time and labor.

According to the method using the capillary apparatus, on the other hand, the quantity of injected samples is about one hundredth of the samples stored in the sample container, with a great majority remaining unused. When the titer plate having holes exhibiting two-dimensional distribution for adjustment of the samples, it has not been possible to utilize the simplified method of controlling the temperature by pressing the capillary against the temperature controlled plate; this has disadvantageously been very inconvenient. Furthermore, electrophoretic injection of samples into the capillary gel to allow them to migrate has disadvantageously resulted in the tip end being damaged, which cannot be re-used.

SUMMARY OF THE INVENTION

In face of said problems, an object of the present invention is to solve the problems of said prior arts, and to provide a sample holding device and method thereof which permit easy injection of the samples into the gel or slab gel in particular in the electrophoresis system.

To attain the above object according to the present invention, sample holding capillaries (a capillary is represented by a capillary tube in the present Specification) are laid out in one or two dimensional array and are made into cartridge, which is used as sample holding device. Samples are held in the capillaries of said sample holding device, and the sample holding capillaries and electrophoresis separation gels are each connected with each other; then electric field is applied thereto and samples are injected.

To be more specific, the sample holding device for electrophoresis apparatus according to the present invention has the functions of (1) holding respective samples (respectively different samples in normal cases) by means of a plurality of capillaries placed in parallel, and of (2) injecting samples into the respectively different migration lanes of the electrophoresis separation part of the electrophoresis apparatus.

The supporting block provided with a plurality of the through holes placed according to a specified layout holds said capillaries in the respective through holes, and the lower ends of the capillaries are allowed to contact the sample injection positions of the electrophoresis separation part of the electrophoresis apparatus. Alternatively, a plurality of plates having a specified thickness with said capillaries held in the through holes may be arranged in the longitudinal direction of the slender flexible film to ensure that the longitudinal direction of the capillary will perpendicularly cross that of the flexible film, and may be immobilized at specified intervals.

The sample holding capillaries can be freely attached or detached from the through holes of the supporting block by friction coupling. Alternatively, a plurality of the through holes may be arranged in a straight line, and the supporting block may be composed of two block pieces which are segmented at the position where each through hole is separated into two.

The said capillaries may be open capillaries or gel filled capillaries. When the open capillaries are used, samples are preferred to be injected into the electrophoresis part through gel filled capillaries.

Sample injection using said sample holding device can be implemented by electrophoretic sample injection as follows: The sample is held in each capillary of the sample holding device by capillarity, and the sample holding device for electrophoresis apparatus is installed on the electrophoresis apparatus so that the lower ends of the capillaries are allowed to contact the sample infection positions of the electrophoresis separation part of the electrophoresis apparatus; then voltage is applied to carry out electrophoretic sample injection.

This method is applicable to the capillary array electrophoresis apparatus, slab gel electrophoresis separation apparatus, electrophoresis apparatus with the gel formed in a plurality of grooves formed on the plate surface, and all other electrophoresis apparatuses.

The inner diameter of the sample holding capillary is preferred to be from 0.03 to 0.4 mm inclusive. Furthermore, the tube thickness is generally ranges from 0.05 to 0.2 mm inclusive, though there is no restriction whatever. The length of the sample holding capillary is normally 3 to 20 mm inclusive, and that of the gel filled capillary must be 5 to 30 mm inclusive. The block supporting the sample holding capillaries should normally have a thickness of 3 to 20 mm inclusive in the direction of the through holes. The sample holding capillaries arranged in an array are normally located at intervals of 0.4 to 9 mm inclusive.

The sample holding capillaries are composed of glass, quartz, polymer and the like, for example. Said supporting block is made up of Teflon, polymer, resin, mica and the like, for example.

The field intensity of the voltage applied for electrophoretic sample injection is 50 to 300 V/cm inclusive.

The sample holding cartridge can be installed or removed from the electrophoresis apparatus. It is easy to handle for its compact size and allows the samples to be injected automatically by means of an automatic pipetter. Combination of the cartridge with the migration part allows the samples to be injected into all migration lanes simultaneously in a short time. Injection of the sample solution into the sample holding capillaries can also be provided by suction from the lower ends of the capillaries by capillarity.

Furthermore, the capillary array cartridge can be composed of gel filled capillaries, or composition may be configured to allow the samples to be injected from the open capillary via the gel filled capillary, thereby making it possible to restrict within the capillary gel cartridge the gel portion destroyed in electrophoretic sample injection, not in electrophoresis separation part; this permits repeated use of the electrophoresis separation part.

Use of hydrophobic material to make the capillary supporting block prevents the sample solution from entering the gap formed by the supporting blocks placed on top of one another.

If the sample holding capillaries of the capillary array cartridge are composed of open capillaries alone, the reaction inside the capillary can be carried out or a specified amount of samples can be picked up and loaded into the capillary array, merely by dipping the capillary into the sample adjusted by the titer plate.

When the present invention uses for adjusting the sample the titer plate having holes exhibiting 2-dimensional distribution, sample injection is performed by allowing the capillaries to be held by the supporting block having the through holes formed in a linear array, after the sample in the titer plate has been put into each capillary. This results in the samples being injected into the electrophoresis separation slab gel or electrophoresis separation gel capillaries having the tube end of the one-dimensional arrangement (linear arrangement); then the separation gel contacts with the temperature controlled plate, thereby ensuring temperature control of electrophoresis separation gel. It is apparent that, when the temperature controlled plate is not used for temperature control, the titer plate having holes exhibiting 2-dimensional distribution is used, samples can be injected into the electrophoresis separation gel capillaries having the tube end of the 2-dimensional arrangement.

BRIEF DESCRIPTION OF THE DRAWINGS

FIG. 4b is a side view representing the sample holding capillary cartridge of FIG. 4a;

DETAILED DESCRIPTION OF PREFERRED EMBODIMENTS

Application of the present invention can be broadly classified into two types; slab gel sample injection and capillary array sample injection. The following describes the details of both of them with reference to embodiments:

Embodiment 1

The present embodiment relates to the slab gel. In the conventional slab gel, samples have been injected into the wells enclosed by glass plate and gel formed on the top of the conventional slab gel. Each well is isolated by gel, however, insufficient gel strength has make it very difficult to decrease the space between wells. Another disadvantage is that the gel once used cannot be used again because the wells are deformed.

Figure 1:
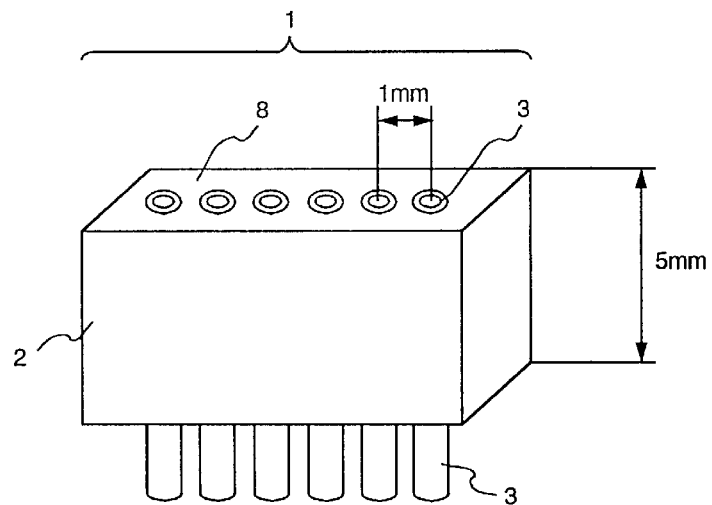
FIG. 1 is a perspective view representing a sample holding capillary cartridge in the first embodiment.

The present embodiment uses the sample holding capillary cartridge 1 illustrated in FIG. 1. In this example, capillary 3 is inserted in the holes on the glass or acryl resin block 2 (5 mm thick) and the surface 8 is ground; this is used as the sample holding capillary cartridge 1.

This embodiment uses the capillary 3 having an inner diameter of 0.1 mm and an outer diameter of 0.3 mm, and block 2 is provided with holes having a diameter of 0.3 mm are arranged at intervals of 1 mm. These holes may be circular or rectangular. The hole tops are tapered in the form somewhat similar to the funnel.

When the sample solution is mounted on the top of the capillary, it is sucked inside by capillarity, thereby filling the lowest end with sample solution. In this case, use of an automatic pipetter permits automatic injection of samples into each of the capillaries in the sample holding capillary cartridge.

Alternatively, the bottom of the capillary 3 is put into the sample container, and sample solution is sucked by capillarity, thereby injecting the sample. In this case, sample can be sucked with capillary 3 removed from the block 2, and capillary 3 after sample injection can be inserted into the holes of block 2.

Figure 2:
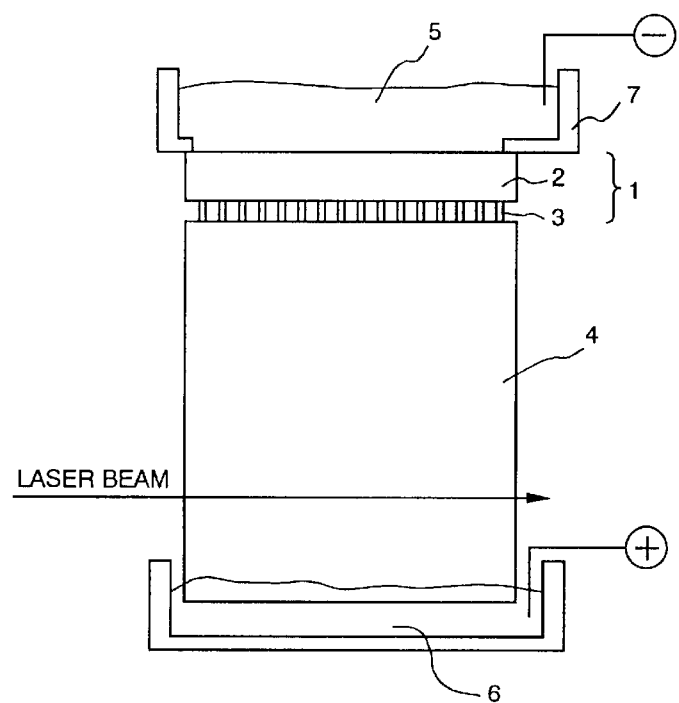
FIG. 2 is a schematic illustration representing the sample holding capillary cartridge in the first embodiment as installed in the electrophoresis apparatus.

FIG. 2 illustrates the connection between the sample holding capillary cartridge and slab gel. The cartridge 1 is installed on the slab gel 4, and the bottom of each capillary 3 injected with samples is made to contact the top of the slab gel 4. Then the top of the cartridge is filled with buffer solution 5, to which electric field is applied. The cartridge top can be filled with the buffer solution, for example, by attaching onto the block 2 of the cartridge 1 under water tight condition the casing 7 provided with opening on the bottom thereof via the O-ring, or by providing the top of the block 2 with a dent to store buffer solution 5. Voltage of 1.4 kV is applied to both ends of the slab plate, and 100-volt voltage is applied to the upper and lower ends of the capillary cartridge for about five seconds to inject the sample into the gel. After injecting the sample into the gel, the cartridge may be removed so that buffer solution 5 is brought in direct contact with the slab gel 4.

Alternatively, electrophoresis may be carried out with the cartridge remaining in position. The bottom of the gel 4 is in contact with the buffer solution 6 to serve as a bottom end for application of electric field. The sample injected into the gel is made to migrate and is separated by the voltage applied across the gel. The position a specified distance away from the migration starting position is irradiated by laser beam to detect the fluorescence emitted from the sample passing thereby.

Figure 3:
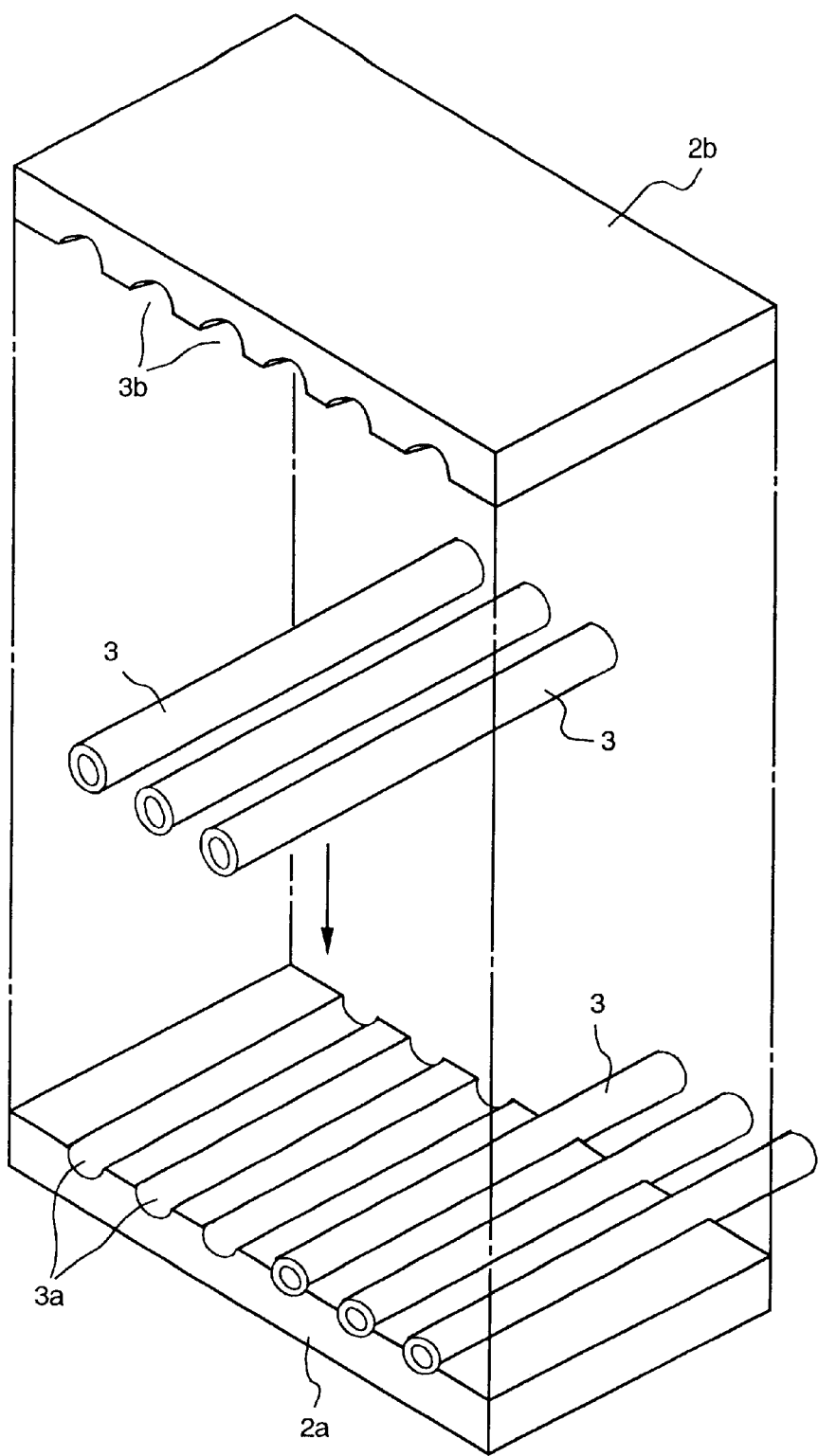
FIG. 3 is a perspective view representing another sample holding capillary cartridge in the first embodiment.

FIG. 3 shows a variation of the sample holding capillary cartridge shown in FIG. 1. This cartridge comprises the blocks 2a and 2b split into two segments and capillaries 3. The split surface of the blocks 2a, 2b of the cartridge are provided with the grooves 3a, 3b to accommodate the capillaries 3. Each capillary 3 is put into the sample solution to suck sample by capillarity, and is then placed on the groove 3a on the block 2a split into two. After that, blocks 2a and 2b are integrated to form a cartridge.

Figure 4A:
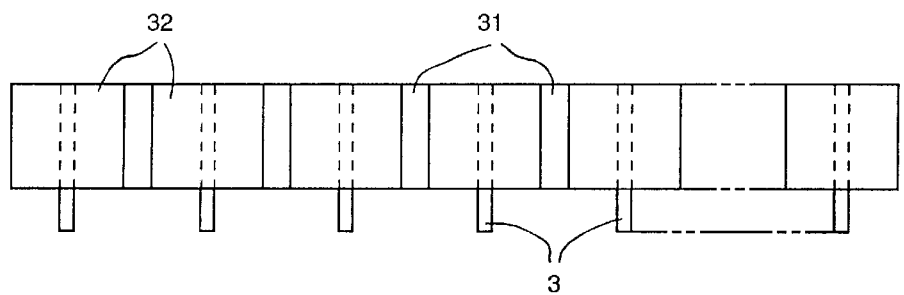
FIG. 4a is a plan view representing still another sample holding capillary cartridge in the first embodiment.
Figure 4B:
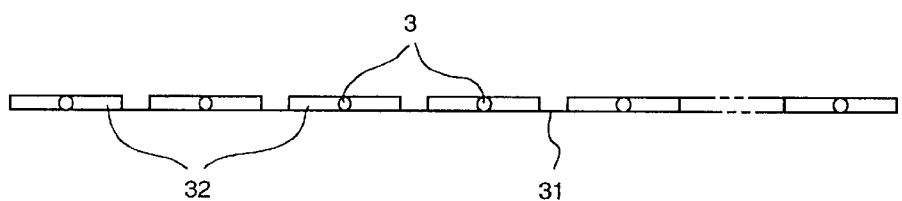

FIGS. 4a and 4b illustrates another example of the sample holding capillary cartridge; FIG. 4a is a plan view while FIG. 4b is a side view. This cartridge is made up, for example, of a plurality of the plates 32 having a thickness of 0.5 mm made of the acryl resin or Teflon (registered trade name) bonded onto the flexible film 31 having a thickness of about 0.02 mm, and capillaries 3 inserted in holes provided in parallel on the surface of the plate 32.

Figure 5A:
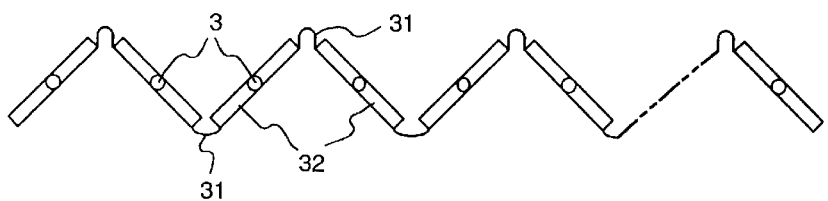
FIGS. 5a and 5b illustrate the method of using the sample holding capillary cartridge of FIGS. 4a and 4b.
Figure 5B:
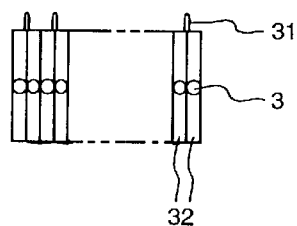

FIGS. 5a and 5b illustrate the sample holding capillary cartridge given in FIGS. 4a and 5b. This cartridge can be folded at the portion of the flexible film between the plates 32 adjacent to this cartridge, and the distance between adjacent capillaries 3 can be changed freely, depending on the degree of this folding. Accordingly, when a plurality of sample solutions placed on the titer plate are injected in respective capillaries 3, for example, it is possible to carry out simultaneous injection of a plurality of sample solutions by folding so that the spacing between capillaries 3 will be equal to that of sample wells in the titer plate, as illustrated in FIG. 5a. After sample injection into capillaries 3, adjacent plates 32 are made to contact with one another, as illustrated in FIG. 5b; then the spacing between the capillaries 3 holding the sample solutions becomes about 1 mm, and samples can be injected into the slab gel, as in the case of the sample holding capillary cartridge shown in FIG. 1.

At the time of electrophoretic sample injection into the gel using the sample holding capillary cartridge illustrated in FIGS. 3, 4a, 4b, 5a and 5b, the voltage can be applied by inserting the needle electrodes into capillaries 3.

Embodiment 2

The present embodiment relates to the capillary array type electrophoresis apparatus.

Figure 6:
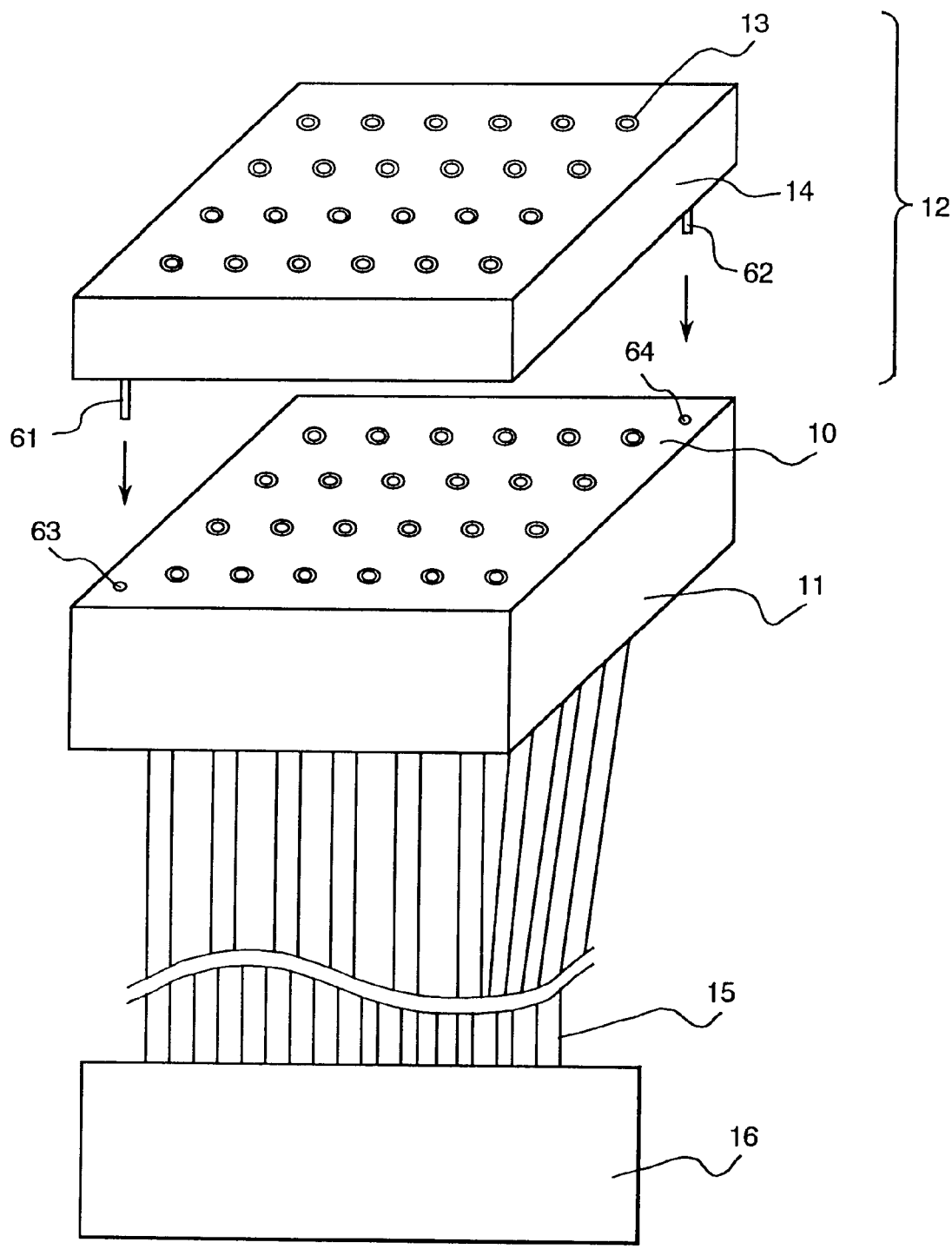
FIG. 6 is a schematic illustration representing the capillary array using the sample holding capillary cartridge in the second embodiment.

FIG. 6 shows an example of the capillary array device equipped with the sample injection part according to the present invention. The tip 10 of the gel capillary array 15 of the electrophoresis separation part on the sample injection side is distributed in two dimensions and, and is supported by the supporting plate 11 made of hydrophobic plastic material such as Teflon (tradename registered), as illustrated in FIG. 6. Use of hydrophobic plastic material to manufacture the supporting plate 11 is intended to ensure that the sample will not be held on the surface of the supporting plate. The supporting plate 11 is provided with holes having a diameter corresponding to the outer diameter of the capillaries of the electrophoresis separation part. Each capillary of the gel capillary array 15 is inserted into each of these holes and is held by friction to ensure that the tip of the capillary will be level with the top of the supporting plate 11.

The sample injection capillary cartridge 12 is composed of the sample holding capillary 13 and the supporter 14 comprising hydrophobic material such as Teflon, and serves to ensure that the sample holding capillary 13 will be arranged in the same layout as the tip 10 on the sample injection side of the gel capillary array 15. After filling the sample holding capillary 13 with the gel and injecting the sample therein, the capillary 13 is placed on top of the supporting plate 11, and is connected with the separation gel capillary 15. Positioning of the supporting plate 11 and the supporter 14 is performed by inserting the pins 61 and 62 of the supporter 14 into the holes 63 and 64 provided on the supporting plate 11. The thickness of the supporter 14, that is the length of the sample holding capillary 13 is 0.5 to 2 cm inclusive. The sample holding capillary 13, is inserted into the holes provided on the supporter 14, and is held in that position by friction. Numeral 16 denotes the measurement part of the capillary array.

The upper part of the sample holding capillary cartridge 14 is filled with the buffer solution as in the case of Embodiment 1, and electric field (150V/cm) is applied to cause electrophoresis. Since fragments migrate from the sample holding capillary 13 to the separation part capillary 15 sequentially starting from the shortest fragment, ensuring electrophoresis for a proper length of time prevents the long fragments in the sample or template DNA from being injected into the capillaries of the separation part. In several minutes, the sample holding capillary cartridge 12 is removed, and electric field is applied to the separation part capillaries to continue electrophoresis separation; then the template DNA and long DNA fragments obtained in complementary chain extending reaction (sequence reaction) remain in the sample injection capillary 13; thus, the signals appearing in the measured DNA fragment spectra can be reduced to zero at a specified fragment length or more. This ensures the repeated measurements without being mixed with the signals of the previous samples, despite repeated injection of the samples into the same gel capillaries.

Furthermore, the sample contains almost no salt. Compared with the gel containing a lot of salt, the electric resistance is high. This provides a high electric resistance in the area where the sample is present in the initial phase of electrophoresis, and high voltage is applied to the shorter part; as a result, the gel close to the sample injection site may be damaged by heat generation, making it impossible to make a repeated use of the same gel. According to the present embodiment, the damaged site is located inside the sample holding capillary, without the possibility of the gel of the electrophoresis part being damaged. This allows repeated use of electrophoresis separation part gel.

The gel used in the sample holding capillary may be agarose, N-isopropylacrylamide gel or the similar material which is turned into liquid with the reticular structure changed by heat generation. In this case, if the solution containing DNA is made to migrate through the capillary filled with this gel, the DNA is trapped in the gel because of its larger molecular size, and salts can be removed there; this makes it possible to concentrate the DNA in this gel. Then it is connected with the separation capillary and is made to migrate by raising the temperature; this allows the DNA to be concentrated to enter the separation part with high efficiency.

The sample migrating inside the gel capillary array 15 is measured by the capillary array measuring part 16. As disclosed in said U.S. Pat. Nos. 5,277,780 and 5,336,608 and Japanese Patents Laid-open No.6-138037 (1994) and No.5-72177 (1993), simultaneous measurement of all capillaries may be made using one or more immobilized laser beams, or each capillary may be measured in sequence through scanning by laser beam.

The behavior of the DNA fragments in the gel has been examined in details using the slab gel [e.g. said Kambara et al; Bio/Technology, vol. 6, pp. 816–821 (1988)]. Electrophoresis by 22 cm in the 6% polyacrylamide at the field intensity of 50 V/cm requires About 4 hours in the case of the 400 bases long DNA. Electrophoresis time is inversely proportional to the electric field and is proportional to the gel length. Thus, when electric field (150V/cm) is applied to a 1 cm sample holding capillary, the 400 bases long DNA enters the separation gel capillaries at the rate of 4 min. or less. Assume that the length of the separation gel capillary is l, the length of the sample holding gel capillary is $\Delta t$, and the time required to remove the sample holding gel capillary is $t_0$ min. The field intensity and gel concentration is assumed to be the same at both of separation and sample holding gel capillaries; then the last long DNA having entered the separation gel capillary reaches the measuring part in $t=(l.t_0/\Delta l)$ minutes.

This allows the next sample to be injected after "t" minutes. When "l" is 25 cm and gel concentration is 6%, "t" is about 90 minutes. That is, this allows sample injection and measurement to be repeated every 90 minutes. Reduction in gel concentration leads to shorter electrophoresis time. This allows one and the same gel to be used for ten times or more. A robot used for installation and removal of the sample injection part will provide a base sequencing capacity of 4K bases per day per capillary, namely, a total of 400K bases per day in terms of 100 bundled capillary arrays.

Figure 7:
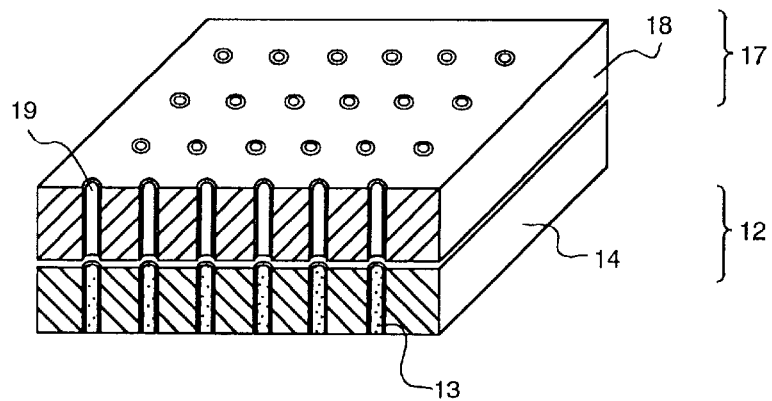
FIG. 7 is a schematic perspective illustration representing the method of injecting the samples into the sample holding capillary cartridge in the second embodiment.

Electrophoretic sample injection is used to introduce samples into the sample holding capillaries. As illustrated in FIG. 7, the sample is held in the open capillary 19 and is connected to the top of the sample holding capillary 13 inside the cartridge; then voltage is applied to perform electrophoretic sample injection. As discussed previously, electric field may be applied via the buffer solution. Alternatively, the needle electrode may be inserted into the open capillary 19. The open capillary 19 is held by the cartridge 17 having the same structure as that of the sample holding capillary cartridge 12, and is bonded placed on top of the sample holding capillary cartridge 12. To inject the sample into the open capillary 19, the sample is placed on the top and is filled into the capillary by capillarity. It is apparent that capillaries may be dipped into the sample solution stored in the sample container to suck the sample by capillarity, thereby storing it into the cartridge. It is also possible to connect it directly to the tip of the separation capillary. Numerals 14 and 18 in FIG. 7 denote supporters.

Embodiment 3

Figure 10:
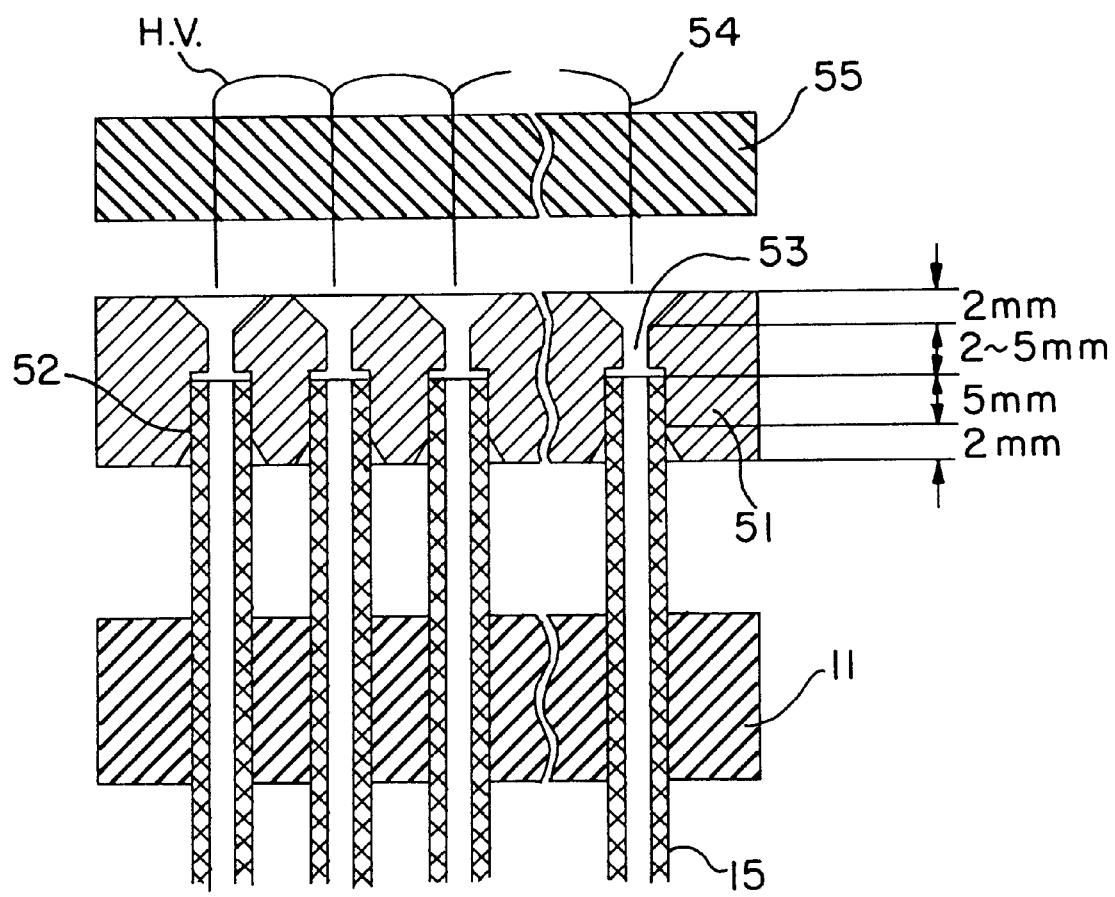
FIG. 10 is a schematic cross sectional view representing the state in which the sample holding capillary cartridge in the third embodiment is installed on the migration capillary.

The sample holding part disposed 2-dimensionally was used in Embodiment 2 to inject the sample into the electrophoresis separation gel capillary. It is also possible to use the sample holding part disposed linearly as in the present Embodiment. FIG. 10 illustrates the present Embodiment as one example. The electrophoresis separation capillaries 15 are bundled in a sheet and are held by the supporting plate 11. The sample injection parts are arranged linearly at intervals of about 1.5 mm. The polyimide coated tube produced by Polymicrotechnology Inc. in the United States was used as capillary 15. Capillary 15 has an inner diameter of 0.1 mm and outer diameter of 0.2 mm. The sample holding cartridge 51 is designed in such a way that the acryl plate having a thickness of 11 to 14 mm inclusive (the plate made of other resin or metallic material may be used) is provided with the holes comprising the sample holding part 53 having a diameter of 0.1 to 0.2 mm inclusive and a length of 2 to 5 mm inclusive, and the capillary guide 52 having a diameter of 0.2 to 0.3 mm inclusive and a length of about 5 mm. To ensure easy sample injection and insertion of the capillary 15, both ends of each hole are tapered, as the diameter being greater at the position closer to the end. The sample is injected into the hole as the sample holding part 53, and the sample holding cartridge 51 is fixed to a cartridge holder (not illustrated). The end of the array of the electrophoresis separation capillary 15 is located on the lower side of the sample holding cartridge 51. Furthermore, a group of the electrodes 54 lined at the same pitch as that of the holes of the sample holding part 52 and the capillary guide 52 are supported by the electrode holder 55 on the upper sides of the sample holding cartridge 51. The sample holding cartridge 51 and the electrode holder 55 are slide so that the electrophoresis separation capillary 15 and the electrode 54 contact the sample in the sample holding part 53; then electric field is applied on the capillaries to inject the sample electrophoretically into the gel in the electrophoresis separation capillary 15.

It is obvious that the inner diameter of the sample holding capillary may be made greater than the outer diameter of the separation gel capillary, and the end of the gel capillary may be partially inserted into the sample holding capillary, thereby injecting the sample.

The sample holding capillaries are not used in the present embodiment, but the similar effects as those obtained by sample holding capillaries are obtained by utilizing the sample holding cartridge 51 having unique holes, as stated above.

The inner diameter of the hole of the sample holding part 53 of the sample holding cartridge 51 shown in the present embodiment should normally be within the range of the outer or inner diameter of the electrophoresis separation capillary 15. The inner diameter of the capillary guide 52 is normally about the outer diameter of the capillary 15 to 0.1 mm larger than that so that the capillary 15 can be inserted and held therein. The taper on both ends of the hole is only required to ensure easy sample injection and capillary insertion; there is no restriction whatever. The length of the sample holding part 53 is 2 to 5 mm inclusive. The length of the capillary guide 52 is about 5 mm, but is not restricted thereto so long as the capillary 15 is held easily.

In the present embodiment, the sample holding part is disposed linearly, but it may be disposed 2-dimensionally if the capillary guide and electrophoresis separation gel capillary group are aligned.

Embodiment 4

Figure 8:
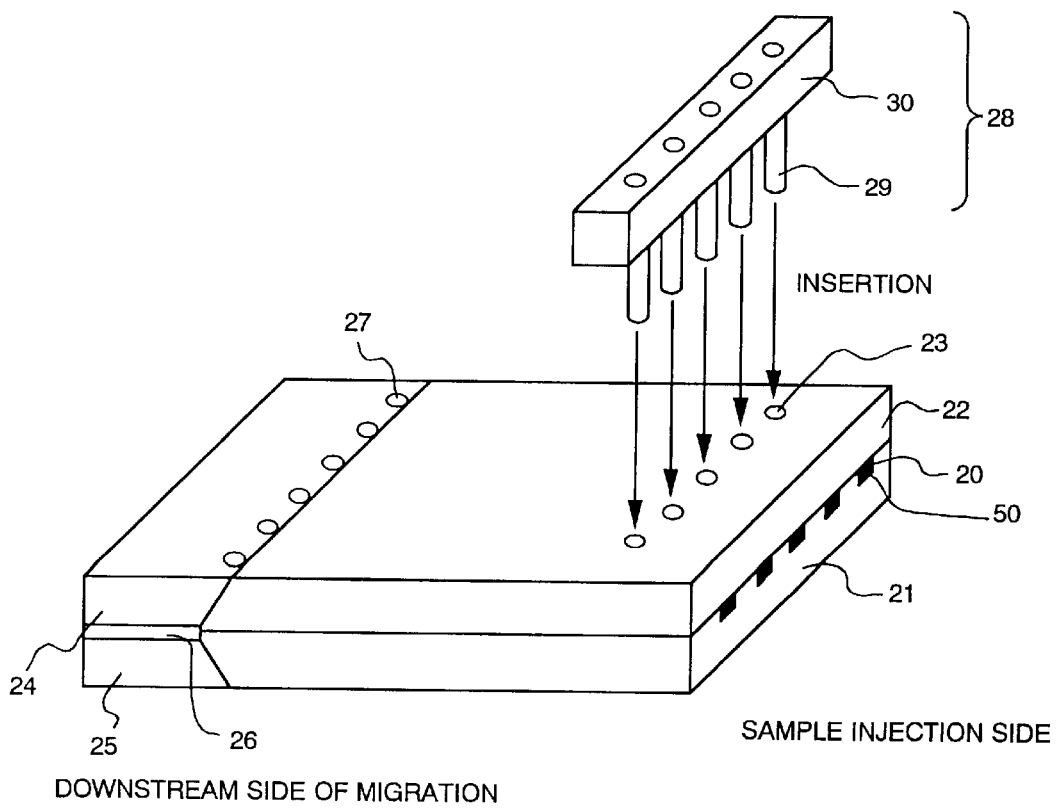
FIG. 8 is a schematic perspective illustration representing electrophoresis apparatus using the sample holding capillary cartridge in the fourth embodiment.

FIG. 8 illustrates an embodiment of applying the present invention to the grooved gel where the finer groove provided on the glass surface is used as electrophoresis capillary. The cross section of the slender groove 20 provided on the quartz plate 21 as the glass plate is 0.5 mm wide and 0.2 mm deep with a pitch of 1 mm. The quartz plate 21 equipped with the slender groove 20 and flat quartz plate 22 are put together to form the capillary migration lane, which is filled with gel 50. The quartz plate is held horizontal and the sample injection window 23 is provided on the sample injection side of the flat quartz plate 22. The downstream side of the groove is connected to a gap space 26 of 0.1 to 0.2 mm width filled with buffer solution. The space is sandwiched with two quartz plates 24 and 25 having flat surfaces. The sample being eluted from the gel end migrates into the gap space 26, where the buffer solution injected from the buffer solution injection port 27 flows in a laminar flow, which prevent the DNA band to diffuse. Furthermore, laser beam is irradiated in the flow channel to allow fluorescent measurement. Laser beam is irradiated on the gap space 26 along the quartz plane as in the case of Embodiment 1, or the laser beam from the position perpendicular to the plane is scanned.

The sample is held inside the capillary 29 of the gel capillary cartridge 28 as in Embodiment 2, and the capillary 29 is inserted into the sample injection window 23. Voltage is applied between the capillary and the downstream end for electrophoresis to inject the sample into the separation gel 50. The present embodiment uses the open capillary or gel capillary as the sample holding capillary 29. The gel capillary also serves to prevent the gel in the separation gel capillary from being damaged. In FIG. 8, the reference numeral 30 denotes a supporter for capillary 29.

Figure 9:
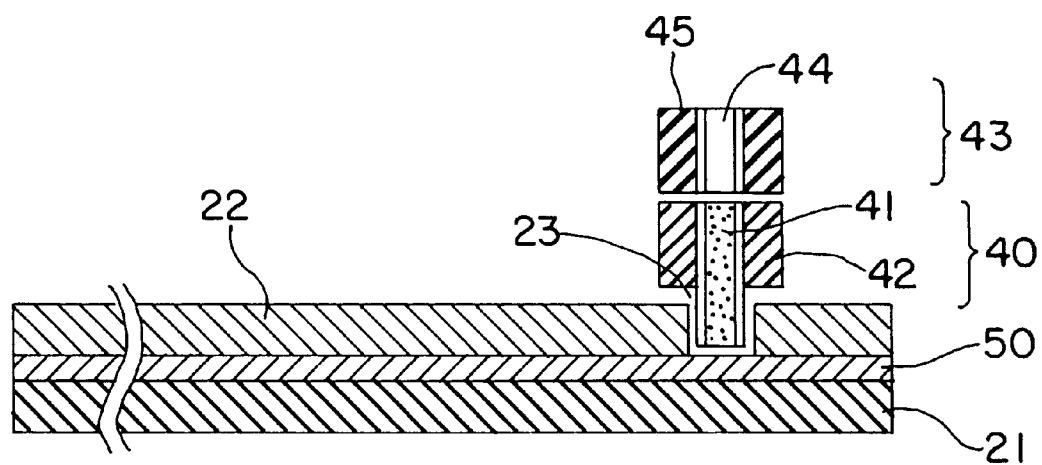
FIG. 9 is a schematic cross sectional view representing electrophoresis apparatus provided with another sample holding capillary cartridge in the fourth embodiment.

When the sample is held by the open capillary and is injected, the gel in the separation part is likely to be damaged, so gel cartridge 40 is placed between open capillary cartridge 43 and the separation gel part, as illustrated in FIG. 9. Where, detachable capillaries 41 are put in the cartridge 40. This is effective in preventing the gel of the analysis part from damage. In this case, supporters 42 and 45 are preferably made of hydrophobic materials such as Teflon. The cartridge 40 comprises the gel capillaries 41 inserted into the holes provided on the supporter 42, while the open cartridge 43 is composed of the open capillaries 44 inserted into the holes provided on the supporter 45. Each capillary is held in each hole by friction. When the composition is as shown in FIG. 9, the gel inside the gel cartridge 40 is damaged by high voltage applied in the initial stage of electrophoresis, without separation gel 50 being damaged. This allows repeated use of electrophoresis separation gel 50.

In another example, this gel can be composed of gel soluble by heating. First, the capillary cartridge holding the sample is put on the gel filled capillary cartridge. Then a high electric field is applied on the capillaries for connecting sample in the gel through electrophoresis. Then the sample holding gel cartridge is put on the top of the separation capillaries, and temperature is raised to make the sample holding gel dissoluble, causing the sample to migrate rapidly to the separation capillary to be injected. In this case, the gel in the gel cartridge constitutes a fine reticular form at low temperature; this does not easily allow the DNA sample to pass by. When temperature is raised, it becomes liquid, allowing the DNA to pass by easily.

Reference numerals 21, 22 and 23 in FIG. 9 denote the quartz plate provided with slender grooves, flat quartz plate, and sample injection window, respectively, as in FIG. 8.

In the above figures, the same numerals denote virtually the same parts unless otherwise specified.

As discussed above, the sample holding capillary cartridge is connected to the electrophoresis separation part to carry out electrophoretic sample injection, according to the present invention. This ensures very easy sample injection. Furthermore, in capillary electrophoresis, gel breakdown is likely to occur around the sample injection end, preventing re-use of the gel separation plate. The analysis gel is protected and repeated use is possible by filling the sample holding capillaries with gel or installing the detachable gel capillaries between the gel and analysis gel capillaries, resulting in considerable improvement in operability.

What is claimed is:

1. A sample injecting device for an electrophoresis apparatus comprising
   a plurality of capillaries with both ends opened are held in a support,
   samples are held in said capillaries, and
   capillary ends opposite to electrode insertion sides are capable of contacting electrophoresis separation parts of the electrophoresis apparatus.

2. A sample injecting device according to claim 1, wherein said capillaries are open capillaries.

3. A sample injecting device according to claim 1, wherein said capillaries are gel filled capillaries.

4. An electrophoresis apparatus comprising:
   a capillary array electrophoresis separation part consisting of a capillary array; and
   a sample injecting device according to claim 1;
   wherein a sample introducing end of said capillary array is held in through holes provided in said sample injecting device in a specified sequence.

5. An electrophoresis apparatus comprising:
   a slab gel electrophoresis separation part; and
   a sample injecting device according to claim 1.

6. An electrophoresis apparatus comprising:
   a electrophoresis separation part consisting of a plurality of grooves formed on a surface of a plate, the grooves being filled with an electrophoresis medium; and
   a sample injecting device according to claim 1.

7. A method for injecting samples into an electrophoresis apparatus comprising the steps of:
   holding samples in the capillaries of a sample injecting device according to claim 1;
   mounting the sample injecting device on the electrophoresis apparatus so that a lower end of each capillary will contact an electrophoresis separation part of the electrophoresis apparatus; and
   applying a voltage to the sample injecting device to carry out electrophoretic sample injection into the electrophoresis separation part of the electrophoresis apparatus.

8. A sample injecting device for an electrophoresis apparatus comprising:
   a supporting block having a plurality of through holes disposed at a specified interval; and
   a plurality of capillaries with both ends opened held in said through holes;
   wherein samples are held in said capillaries; and
   wherein capillary ends opposite to electrode insertion sides are capable of contacting an electrophoresis separation part of the electrophoresis apparatus.

9. A sample injecting device according to claim 8, wherein said capillaries are held in said through holes so that they can be removed and reinstalled as required.

10. A sample injecting device according to claim 8, wherein openings formed by said capillaries passing through surfaces of said supporting block are arranged in straight line.

11. A sample injecting device according to claim 10, wherein said supporting block can be split in two in a longitudinal direction along said through holes.

12. A sample injecting device for an electrophoresis apparatus wherein a plurality of plates having capillaries holding samples and having a specified thickness are laid out and fixed on a slender flexible film at specified intervals so that a longitudinal direction of said capillaries perpendicularly crosses a longitudinal direction of said slender flexible film.

13. A sample injecting device for an electrophoresis apparatus comprising:

first means consisting of open capillaries held in a plurality of through holes disposed linearly or two-dimensionally in a first hydrophobic supporting block; and second means consisting of gel filled capillaries held in a plurality of through holes which are laid out in a second hydrophobic supporting block to match up with the through holes in said first hydrophobic supporting block;

wherein said first means can be mounted on said second means with a lower end of each open capillary contacting a top end of a corresponding gel filled capillary, and a lower end of each gel filled capillary can contact a sample injection portion of the electrophoresis apparatus.

14. A sample injecting device for an electrophoresis apparatus comprising:

a plate having formed therein sample holding holes and capillary guide holes, said sample holding holes having a diameter greater than an inner diameter of electrophoresis separation capillaries of the electrophoresis apparatus and a length of 2 to 5 mm inclusive, and said capillary guide holes having a diameter which ranges from an outer diameter of said capillaries to 0.1 mm greater than the outer diameter of said capillaries, said sample holding holes and said capillary guide holes being connected with each other, thereby forming through holes in said plate, both ends of said through holes increasing in diameter as said through holes approach surfaces of said plate.

15. An electrophoresis apparatus comprising:

a sample injecting device according to claim 13; and a plurality of electrophoresis separation capillaries each having an end disposed in a respective one of the capillary guide holes of the sample injecting device.

16. A sample injecting device for an electrophoresis apparatus, the electrophoresis apparatus including a plurality of electrophoresis separation portions into which the sample injecting device electrophoretically injects samples, the sample injecting device comprising:

a plurality of capillaries having respective first ends and respective second ends, the first ends and the second ends being open, the capillaries having samples disposed therein; and capillary holding means for holding the capillaries in an arrangement in which the second ends of the capillaries contact respective ones of the electrophoresis separation portions while the sample injecting device is electrophoretically injecting the samples into the electrophoresis separation portions.

17. A sample injecting device according to claim 16, wherein the capillaries are open capillaries not filled with an electrophoresis medium.

18. A sample injecting device according to claim 16, wherein the capillaries are filled with an electrophoresis medium.

19. An electrophoresis apparatus comprising:

an array of electrophoresis separation capillaries constituting a plurality of electrophoresis separation portions, the electrophoresis separation capillaries having respective sample introduction ends; and a sample injecting device according to claim 16;

wherein the sample introduction ends of the electrophoresis separation capillaries are disposed in the same arrangement in which the capillaries of the sample injecting device are held by the capillary holding means.

20. An electrophoresis apparatus comprising:

an electrophoresis separation slab gel having a plurality of migration lanes constituting a plurality of electrophoresis separation portions, the migration lanes having respective sample introduction ends; and a sample injecting device according to claim 16.

21. An electrophoresis apparatus comprising:

a plate having a plurality of grooves formed therein, the grooves being filled with an electrophoresis medium and constituting a plurality of electrophoresis separation portions; and a sample injecting device according to claim 16.

22. A method of injecting samples into an electrophoresis apparatus, the electrophoresis apparatus including a plurality of electrophoresis separation portions having respective sample injection positions, the method comprising the steps of:

injecting samples into the first ends of the capillaries of a sample injecting device according to claim 16;

mounting the sample injecting device on the electrophoresis apparatus such that the second ends of the capillaries contact respective ones of the sample injection positions; and applying a voltage to the capillaries to electrophoretically inject the samples into the electrophoresis separation portions at the sample injection positions.

23. A sample injecting device for an electrophoresis apparatus, the electrophoresis apparatus including an electrophoresis separation portion into which the sample injecting device electrophoretically injects samples, the sample injecting device comprising:

a plurality of capillaries having respective first ends and respective second ends, the first ends and the second ends being open, the capillaries having samples disposed therein; and a supporting block having a plurality of through holes in which respective ones of the capillaries are disposed, the through holes being arranged in an arrangement in which the second ends of the capillaries contact the electrophoresis separation portion while the sample injecting device is electrophoretically injecting the samples into the electrophoresis separation portion.

24. A sample injecting device according to claim 23, wherein the capillaries are removably disposed in the through holes, thereby enabling the capillaries to be installed in the through holes and removed from the through holes.

25. A sample injecting device according to claim 23, wherein the through holes have respective center lines extending through the through holes; and
wherein the through holes are arranged such that the center lines of the through holes lie in a single plane intersecting opposite surfaces of the supporting block.

26. A sample injecting device according to claim 25, wherein the supporting block is divided into two portions along the single plane; and
wherein the two portions of the supporting block are separable from each other to enable the capillaries to be installed in the through holes and removed from the through holes.

27. A sample injecting device according to any one of claims 23 to 26, wherein the capillaries are open capillaries not filled with an electrophoresis medium.

28. A sample injecting device according to any one of claims 23 to 26, wherein the capillaries are filled with an electrophoresis medium.

29. An electrophoresis apparatus comprising:
an array of electrophoresis separation capillaries constituting an electrophoresis separation portion, the electrophoresis separation capillaries having respective sample introduction ends; and
a sample injecting device according to any one of claims 23 to 26;
wherein the sample introduction ends of the electrophoresis separation capillaries are disposed in the same arrangement in which the through holes of the supporting block of the sample injecting device are arranged.

30. An electrophoresis apparatus comprising:
an electrophoresis separation slab gel constituting an electrophoresis separation portion; and
a sample injecting device according to any one of claims 23 to 26.

31. An electrophoresis apparatus comprising:
a plate having a plurality of grooves formed therein, the grooves being filled with an electrophoresis medium and constituting an electrophoresis separation portion; and
a sample injecting device according to any one of claims 23 to 26.

32. A method of injecting samples into an electrophoresis apparatus, the electrophoresis apparatus including an electrophoresis separation portion, the method comprising the steps of:
injecting samples into the first ends of the capillaries of a sample injecting device according to any one of claims 23 to 26;
mounting the sample injecting device on the electrophoresis apparatus such that the second ends of the capillaries contact the electrophoresis separation portion; and
applying a voltage to the capillaries to electrophoretically inject the samples into the electrophoresis separation portion.

33. A sample injecting device for an electrophoresis apparatus, the sample injecting device comprising:
a plurality of plates;
a plurality of capillaries disposed in respective ones of the plates, the capillaries having samples disposed therein; and
a flexible film having a thickness, a width greater than the thickness, and a length greater than the width;
wherein the plates are attached to the flexible film at intervals along the length of the flexible film such that the capillaries extend parallel to the width of the flexible film and perpendicularly to the length of the flexible film.

34. A sample injecting device according to claim 33, wherein the capillaries are open capillaries not filled with an electrophoresis medium.

35. A sample injecting device according to claim 33, wherein the capillaries are filled with an electrophoresis medium.

36. An electrophoresis apparatus comprising:
an array of electrophoresis separation capillaries; and
a sample injecting device according to claim 33;
wherein the capillaries of the sample injecting device inject the samples into the electrophoresis separation capillaries.

37. An electrophoresis apparatus comprising:
an electrophoresis separation slab gel; and
a sample injecting device according to claim 33;
wherein the capillaries of the sample injecting device inject the samples into the electrophoresis separation slab gel.

38. An electrophoresis apparatus comprising:
a plate having a plurality of grooves formed therein, the grooves being filled with an electrophoresis medium; and
a sample injecting device according to claim 33;
wherein the capillaries of the sample injecting device inject the samples into the grooves.

39. A method of injecting samples into an electrophoresis apparatus, the electrophoresis apparatus including an electrophoresis separation portion having a plurality of sample injection positions, the method comprising the steps of:
injecting samples into first ends of the capillaries of a sample injecting device according to claim 33;
mounting the sample injecting device on the electrophoresis apparatus such that second ends of the capillaries contact respective ones of the sample injection positions; and
applying a voltage to the capillaries to electrophoretically inject the samples into the electrophoresis separation portion at the sample injection positions.

40. A sample injecting device for an electrophoresis apparatus, the electrophoresis apparatus having a plurality of sample injection positions at which the sample injecting device injects samples into the electrophoresis apparatus, the sample injecting device comprising:
a plurality of first capillaries having respective first ends and respective second ends, the first capillaries being open capillaries not filled with an electrophoresis medium;
a first supporting block made of a hydrophobic material and having a plurality of through holes in which respective ones of the first capillaries are disposed, the through holes being arranged in one of a linear arrangement and a two-dimensional arrangement;
a plurality of second capillaries having respective first ends and respective second ends, the second capillaries being filled with an electrophoresis medium, the second capillaries being equal in number to the first capillaries; and
a second supporting block made of a hydrophobic material and having a plurality of through holes in which respective ones of the second capillaries are disposed, the through holes of the second supporting block being arranged in the same arrangement in which the through holes of the first supporting block are arranged;

wherein the first supporting block is mounted on the second supporting block such that the second ends of the first capillaries contact the first ends of respective ones of the second capillaries; and wherein the second ends of the second capillaries contact respective ones of the sample injection positions while the sample injecting device is injecting samples into the electrophoresis apparatus at the sample injection positions.

41. An electrophoresis apparatus comprising:

an array of electrophoresis separation capillaries having respective sample introduction ends, the sample introduction ends constituting respective sample injection positions of the electrophoresis apparatus; and a sample injecting device according to claim 40;

wherein the sample introduction ends of the electrophoresis separation capillaries are disposed in the same arrangement in which the through holes of the second supporting block of the sample injecting device are arranged.

42. An electrophoresis apparatus comprising:

an electrophoresis separation slab gel having a plurality of sample injection positions; and a sample injecting device according to claim 40;

wherein the sample injection positions of the electrophoresis separation slab gel are disposed in the same arrangement in which the through holes of the second supporting block of the sample injecting device are arranged.

43. An electrophoresis apparatus comprising:

a plate having a plurality of grooves formed therein, the grooves being filled with an electrophoresis medium, the grooves having respective sample injection positions constituting sample injection positions of the electrophoresis apparatus; and a sample injecting device according to claim 40;

wherein the sample injection positions of the grooves are disposed in the same arrangement in which the through holes of the second supporting block of the sample injecting device are arranged.

44. A method of injecting samples into an electrophoresis apparatus, the electrophoresis apparatus including an electrophoresis separation portion having a plurality of sample injection positions, the method comprising the steps of:

injecting samples into the first ends of the first capillaries of a sample injecting device according to claim 40;

mounting the sample injecting device on the electrophoresis apparatus such that the second ends of the second capillaries of the sample injecting device contact respective ones of the sample injection positions; and applying a voltage to the first capillaries to electrophoretically inject the samples into the electrophoresis separation portion at the sample injection positions.

45. A sample injecting device for an electrophoresis apparatus, the electrophoresis apparatus including an electrophoresis separation capillary, the sample injecting device comprising:

a plate having a first surface having a first hole formed therein and a second surface having a second hole formed therein, the second hole being connected to the first hole at a junction so as to form a through hole in the plate between the first surface and the second surface;

wherein the first hole has a diameter greater than an inner diameter of the electrophoresis separation capillary at the junction, and flare outs as it approaches the first surface from the junction beginning at a non-zero distance from the junction such that the first hole has a diameter at the first surface which is greater than the diameter of the first hole at the junction;

wherein the second hole has a diameter greater than an outer diameter of the electrophoresis separation capillary at the junction, and flare outs as it approaches the second surface from the junction beginning at a non-zero distance from the junction such that the second hole has a diameter at the second surface which is greater than the diameter of the second hole at the junction;

wherein a sample is injected into the first hole; and wherein an end of the electrophoresis separation capillary is inserted into the second hole to enable the sample injecting device to inject the sample into the electrophoresis separation capillary.

46. An electrophoresis apparatus comprising:

an array of electrophoresis separation capillaries; and a sample injecting device according to claim 45;

wherein the plate of the sample injecting device has a plurality of the through holes respectively corresponding to the electrophoresis separation capillaries.

47. A method of injecting samples into an electrophoresis apparatus, the electrophoresis apparatus including an electrophoresis separation capillary, the method comprising the steps of:

injecting samples into the first hole of the plate of a sample injecting device according to claim 45;

mounting the sample injecting device on the electrophoresis apparatus such that an end of the electrophoresis separation capillary is inserted into the second hole of the plate of the sample injecting device; and applying a voltage to the plate to electrophoretically inject the sample into the electrophoresis separation capillary.

48. A real time fluorescence detecting electrophoresis apparatus comprising:

a plurality of migration lanes having respective sample injection positions; and a plurality of capillaries filled with an electrophoresis medium for electrophoretically injecting samples into respective ones of the migrations lanes at the sample injection positions.

49. A real time fluorescence detecting electrophoresis apparatus comprising:

a slab having a plurality of migration lanes, the migration lanes having respective sample injection positions; and a plurality of capillaries filled with an electrophoresis medium for electrophoretically injecting samples into respective ones of the migration lanes at the sample injection positions.

50. A real time fluorescence detecting electrophoresis apparatus comprising:

a plurality of first capillaries filled with an electrophoresis medium, the first capillaries having respective sample injection positions; and a plurality of second capillaries filled with an electrophoresis medium for electrophoretically injecting samples into respective ones of the first capillaries at the sample injection positions.

51. A real time fluorescence detecting electrophoresis apparatus comprising:

a first plate having a plurality of grooves formed therein, the grooves being filled with an electrophoresis medium;

a second plate covering the grooves in the first plate, thereby forming a plurality of first capillaries corresponding to the grooves, the first capillaries having respective sample injection positions; and a plurality of second capillaries filled with an electrophoresis medium for electrophoretically injecting samples into respective ones of the first capillaries at the sample injection positions.

52. A real time fluorescence detecting electrophoresis apparatus comprising:

a first plate having a plurality of grooves formed therein, the grooves being filled with an electrophoresis medium;

a second plate covering the grooves in the first plate, thereby forming a plurality of first capillaries corresponding to the grooves, the first capillaries having respective sample introducing positions; and a plurality of second capillaries filled with an electrophoresis medium holding samples therein and being held in a plurality of through holes disposed linearly in a supporter;

wherein ends of the second capillaries contact the sample introducing portions, and the samples are transferred from the ends of the second capillaries to the sample introduction portions.

53. A real time fluorescence detecting electrophoresis apparatus comprising:

a first plate having a plurality of grooves formed therein, the grooves being filled with an electrophoresis medium;

a second plate covering the grooves in the first plate, thereby forming a plurality of first capillaries corresponding to the grooves; and a plurality of second capillaries holding samples therein and being held in a plurality of through holes disposed linearly in a supporter;

wherein ends of the second capillaries contact the first capillaries, and the samples are transferred from the ends of the second capillaries to the first capillaries.

54. A method of transferring samples into an electrophoresis apparatus, the electrophoresis apparatus including a plurality of electrophoresis separation portions having respective sample introducing positions, the method comprising the steps of:

injecting samples into capillaries of sample transferring device, said capillaries filled with a gel;

mounting the sample transferring device on the electrophoresis apparatus such that the ends of the capillaries contact respective ones of the sample introducing positions;

raising temperature of said capillaries to change an electrophoresis condition of the samples in the gel; and applying a voltage to the capillaries to electrophoretically transfer the samples into the electrophoresis separation portions at the sample introducing positions.

55. A sample transferring device for an electrophoresis apparatus including a plurality of electrophoresis separation portions, the sample transferring device comprising:

a plurality of open capillaries holding samples and being held in a plurality of through holes disposed linearly in a supporter; and first and second electrodes each disposed in different vessel for transferring the samples from said capillaries into the electrophoresis separation portions;

wherein the samples are transferred electrophoretically from said capillaries into the electrophoresis separation portions.

56. A sample transferring device for an electrophoresis apparatus including a plurality of electrophoresis separation portions having respective sample introducing positions, the sample transferring device comprising:

a plurality of gel filled capillaries holding samples and being held in a plurality of through holes disposed linearly or two-dimensionally in a supporter; and first and second electrodes each disposed in different vessel for transferring the samples from said capillaries into the separation portions at the sample introducing positions;

wherein the samples are transferred electrophoretically from said capillaries into the electrophoresis separation portions at the sample introducing positions.

57. A sample transferring device for an electrophoresis apparatus comprising:

a plurality of capillaries disposed on a flexible film at a preset interval, the capillaries holding samples;

wherein an interval between adjacent ones of the capillaries is changeable by folding the flexible film.

58. A method of transferring samples into an electrophoresis apparatus, the electrophoresis apparatus including a plurality of electrophoresis separation portions having respective sample introducing positions, and a sample transferring device including a plurality of capillaries disposed on a flexible film at a preset interval, the method comprising the steps of:

changing an interval between adjacent ones of the capillaries by holding the flexible film of said sample transferring device so that the interval between adjacent ones of the capillaries is equal to an interval between sample wells in a sample holding plate;

transferring samples from the sample wells to the capillaries;

changing the interval between adjacent ones of the capillaries by holding the flexible film of said sample transferring device so that the interval between adjacent ones of the capillaries is equal to an interval between said sample introducing positions;

mounting the sample transferring device on the electrophoresis apparatus such that ends of the capillaries contact the sample introducing positions; and transferring the samples from the capillaries to the electrophoresis separation portions at said sample introducing positions;

wherein the interval between the sample wells is different from the interval between the sample introducing positions.

59. A sample transferring device for an electrophoresis apparatus, the electrophoresis apparatus including a plurality of sample introducing portions, the sample transferring device comprising:

a supporter having a plurality of through holes, the through holes being disposed in a two-dimensional arrangement; and a plurality of capillaries filled with an electrophoresis medium and holding samples therein, the capillaries being disposed in the through holes of the supporter;

wherein one end of each of the capillaries contacts a corresponding one of the sample introducing portions of the electrophoresis apparatus so that the samples are transferred from the capillaries to the sample introducing portions of the electrophoresis apparatus.

60. A sample transferring device for an electrophoresis apparatus, the electrophoresis apparatus including a plurality of sample introducing portions, the sample transferring device comprising:

a first supporter having a plurality of through holes, the through holes being disposed in one of a linear arrangement and a two-dimensional arrangement;

a plurality of first capillaries holding samples therein, the first capillaries being disposed in the through holes of the first supporter;

a second supporter having a plurality of through holes, the through holes being disposed in a same one of a linear arrangement and a two-dimensional arrangement as the through holes of the first supporter so that the through holes of the first supporter match up with the through holes of the second supporter when the first supporter is mounted on the second supporter; and a plurality of second capillaries filled with an electrophoresis medium, the second capillaries being disposed in the through holes of the second supporter;

wherein the first supporter is mountable on the second supporter so that a first end of each of the first capillaries contacts a first end of a corresponding one of the second capillaries to transfer the samples from the first capillaries to the second capillaries; and wherein a second end of each of the second capillaries contacts a corresponding one of the sample introducing portions of the electrophoresis apparatus.

61. A sample transferring device according to claim 60, wherein the through holes of the first supporter and the second supporter are arranged in a two-dimensional arrangement in which the through holes are arranged in a plurality of parallel straight lines.

62. An electrophoresis apparatus comprising:

a supporting block having a plurality of through holes;

a capillary array electrophoresis separation part including a capillary array constituted by a plurality of capillaries disposed in an array, each of the capillaries of the capillary array having a sample introducing end constituting a sample introducing portion of the electrophoresis apparatus, the sample introducing ends of the capillaries of the capillary array being disposed in the through holes of the supporting block; and a sample transferring device according to claim 60.

63. An electrophoresis apparatus comprising:

a gel electrophoresis separation part including a plate having a plurality of grooves formed therein, the grooves being filled with a gel, each of the grooves having a sample introducing end constituting a sample introducing portion of the electrophoresis apparatus; and a sample transferring device according to claim 60.

64. A method of transferring samples into an electrophoresis apparatus including a plurality of sample introducing portions using a sample transferring device according to claim 60, the method comprising the steps of:

injecting samples into a second end of each of the first capillaries of the sample transferring device;

mounting the first supporter of the sample transferring device on the second supporter of the sample transferring device so that the first end of each of the first capillaries of the sample transferring device contacts the first end of the corresponding one of the second capillaries of the sample transferring device;

transferring the samples from the first capillaries of the sample transferring device to the second capillaries of the sample transferring device;

placing the second end of each of the second capillaries of the sample transferring device in contact with the corresponding one of the sample introducing portions of the electrophoresis apparatus; and applying a voltage to the sample transferring device to electrophoretically transfer the samples from the second capillaries of the sample transferring device into the sample introducing portions of the electrophoresis apparatus.

65. A sample transferring device for an electrophoresis apparatus, the electrophoresis apparatus including an electrophoresis separation part, the electrophoresis separation part having a plurality of sample transferring positions, the sample transferring device comprising:

a supporting block having a plurality of through holes, the through holes being disposed at specified intervals; and a plurality of capillaries holding samples therein, the capillaries being removably disposed in the through holes of the supporting block so that they can be removed from the through holes of the supporting block and reinstalled in the through holes of the supporting block, each of the capillaries having a first end constituting an electrode insertion end into which an electrode is inserted, and a second end which contacts a corresponding one of the sample transferring positions of the electrophoresis separation part of the electrophoresis apparatus.

66. A sample transferring device for an electrophoresis apparatus, the electrophoresis apparatus including an electrophoresis separation part, the electrophoresis separation part having a plurality of sample transferring positions, the sample transferring device comprising:

a supporting block having a plurality of through holes, the through holes being disposed in a straight line at specified intervals, the supporting block being separable into two pieces along a plane extending along the straight line and through the through holes; and a plurality of capillaries holding samples therein, the capillaries being open capillaries, the capillaries being disposed in the through holes of the supporting block, each of the capillaries having a first end constituting an electrode insertion end into which an electrode is inserted, and a second end which contacts a corresponding one of the sample transferring positions of the electrophoresis separation part of the electrophoresis apparatus.

67. A sample transferring device for an electrophoresis apparatus, the sample transferring device comprising:

a plurality of plates each having a specified thickness;

a plurality of capillaries disposed in respective one of the plates, the capillaries holding samples therein; and a flexible film having a thickness, a width greater than the thickness, and a length greater than the width;

wherein the plates are attached to the flexible film at specified intervals along the length of the flexible film so that the capillaries extend parallel to the width of the flexible film and perpendicularly to the length of the flexible film.

68. A sample transferring device for an electrophoresis apparatus, the electrophoresis apparatus including an electrophoresis separation part, the electrophoresis separation part having a plurality of sample transferring positions, the sample transferring device comprising:

a support; and a plurality of capillaries filled with an electrophoresis medium and holding samples therein, the capillaries being disposed in the support, each of the capillaries having a first end constituting an electrode insertion end into which an electrode is inserted, and a second end which contacts a corresponding one of the sample transferring positions of the electrophoresis separation part of the electrophoresis apparatus.

69. A sample transferring device for an electrophoresis apparatus, the electrophoresis apparatus including a plurality of sample introducing portions, the sample transferring device comprising:

a first unit including a first supporting block having a plurality of through holes, the first supporting block being hydrophobic, the through holes being disposed in one of a linear arrangement and a two-dimensional arrangement, and a plurality of first capillaries disposed in the through holes of the first supporting block, the first capillaries being open capillaries; and a second unit including a second supporting block having a plurality of through holes, the through holes being disposed in a same one of a linear arrangement and a two-dimensional arrangement as the through holes of the first supporting block so that the through holes of the first supporting block match up with the through holes of the second supporting block when the first unit is mounted on the second unit, and a plurality of second capillaries filled with an electrophoresis medium, the second capillaries being disposed in the through holes of the second supporting block;

wherein the first unit is mountable on the second unit so that a first end of each of the first capillaries contacts a first end of a corresponding one of the second capillaries; and wherein a second end of each of the second capillaries contacts a corresponding one of the sample introducing portions of the electrophoresis apparatus.

70. An electrophoresis apparatus comprising:

a slab gel electrophoresis separation part having a plurality of sample introducing portions disposed at an upper end of the slab gel electrophoresis separation part;

a sample transferring device which is removable from the slab gel electrophoresis separation part, the sample transferring device including a supporter having a plurality of through holes disposed in a linear arrangement, and a plurality of capillaries holding samples therein, the capillaries being disposed in the through holes of the supporter, each of the capillaries having a lower end which contacts a corresponding one of the sample introducing portions of the slab gel electrophoresis separation part;

an upper vessel containing a buffer solution, the buffer solution in the upper vessel contacting an upper end of each of the capillaries;

a first electrode disposed in the buffer solution in the upper vessel;

a lower vessel containing a buffer solution, the buffer solution in the lower vessel contacting a lower end of the slab gel electrophoresis separation part; and a second electrode disposed in the buffer solution in the lower vessel.

71. A sample transferring device for an electrophoresis apparatus, the electrophoresis apparatus including a plurality of electrophoresis separation capillaries, the sample transferring device comprising:

a plate having a plurality of sample holding holes formed in a first surface of the plate and a plurality of capillary guide holes formed in a second surface of the plate, the sample holding holes being connected with corresponding ones of the capillary guide holes to form through holes between the first surface of the plate and the second surface of the plate;

wherein the sample holding holes have a length of 2 mm to 5 mm, and a diameter which is greater than an inner diameter of the electrophoresis separation capillaries of the electrophoresis apparatus and which increases as the sample holding holes approach the first surface of the plate; and wherein the capillary guide holes have a diameter which is not less than an outer diameter of the electrophoresis separation capillaries of the electrophoresis apparatus, which is not greater than 0.1 mm greater than the outer diameter of the electrophoresis separation capillaries of the electrophoresis apparatus, and which increases as the capillary guide holes approach the second surface of the plate.

72. An electrophoresis apparatus comprising:

a plurality of electrophoresis separation capillaries; and a sample transferring device according to claim 71.

* * * * *